United States Patent
Gustilo et al.

[11] Patent Number: 6,162,257
[45] Date of Patent: Dec. 19, 2000

[54] ACETABULAR CUP PROSTHESIS WITH EXTENSION FOR DEFICIENT ACETABULUM

[76] Inventors: Ramon B. Gustilo; Joan E. Bechtold; Douglas Cooper; Marie Guion; Richard S. Hammett, all of c/o Midwest Orthopaedic Research Foundation, 914 S. Eighth St., 860C, Minneapolis, Minn. 55415-1829

[21] Appl. No.: 09/183,032

[22] Filed: Oct. 30, 1998

Related U.S. Application Data

[60] Provisional application No. 60/063,905, Oct. 31, 1997.

[51] Int. Cl.[7] .................................................. A61F 2/36
[52] U.S. Cl. ........................... 623/22.32; 623/22.38
[58] Field of Search .................. 623/22, 22.32, 623/22.38

[56] References Cited

U.S. PATENT DOCUMENTS

| | | | |
|---|---|---|---|
| 4,883,489 | 11/1989 | Grundei | 623/22 |
| 4,904,265 | 2/1990 | MacCollum | 623/22 |
| 5,030,238 | 7/1991 | Nieder | 623/22 |
| 5,176,711 | 1/1993 | Grimes | 623/22 |
| 5,326,367 | 7/1994 | Robioneck | |
| 5,425,778 | 6/1995 | Zichner | 623/22 |
| 5,458,650 | 10/1995 | Carret | 623/22 |
| 5,658,347 | 8/1997 | Sarkisian | 623/22 |
| 5,702,477 | 12/1997 | Capello | 623/22 |
| 5,871,548 | 2/1999 | Sanders et al. | |
| 5,931,870 | 8/1999 | Cuckler | 623/22 |
| 5,935,175 | 8/1999 | Ostiguy | 623/22 |
| 5,976,149 | 11/1999 | Masini | 623/22 |

*Primary Examiner*—Michael J. Milano
*Attorney, Agent, or Firm*—Patterson, Thuente, Skaar & Christensen, P.A.

[57] ABSTRACT

An acetabular cup prosthesis designed to customize the fit and stability of an acetabular cup in deficient acetabulae without excessive reaming of good bone surrounding the deficiency. The acetabular cup prosthesis generally comprises a cup-shaped body portion, an extension, and a liner. The extension is preferably produced at selected angles, which are appropriate to various acetabular defects, and is designed to connect to the cup-shaped body portion. The body portion and extension are secured to the bone and the liner is inserted within the body portion. Those surfaces of the body portion and extension contacting the surface of the bone are preferably porous surfaces that may have also been coated with a coating to enhance bone growth.

52 Claims, 6 Drawing Sheets

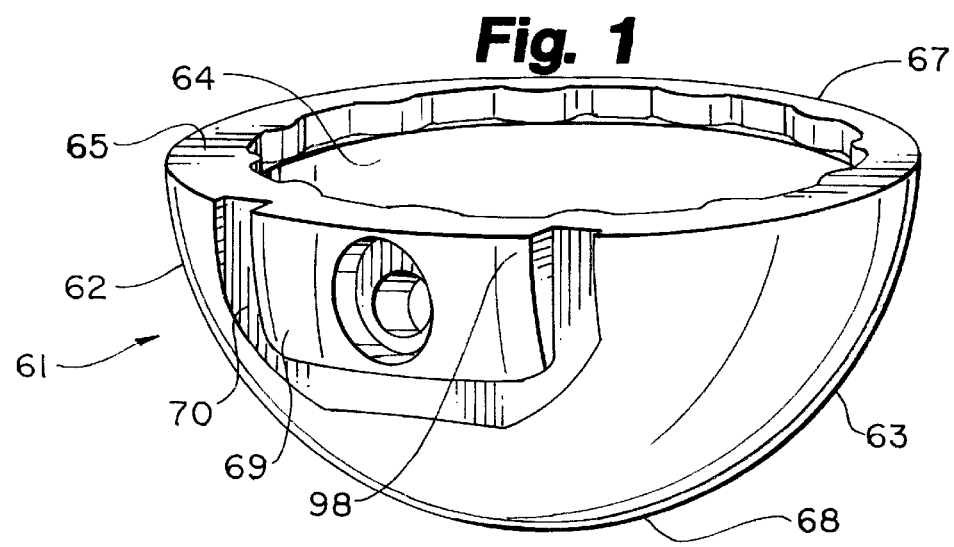
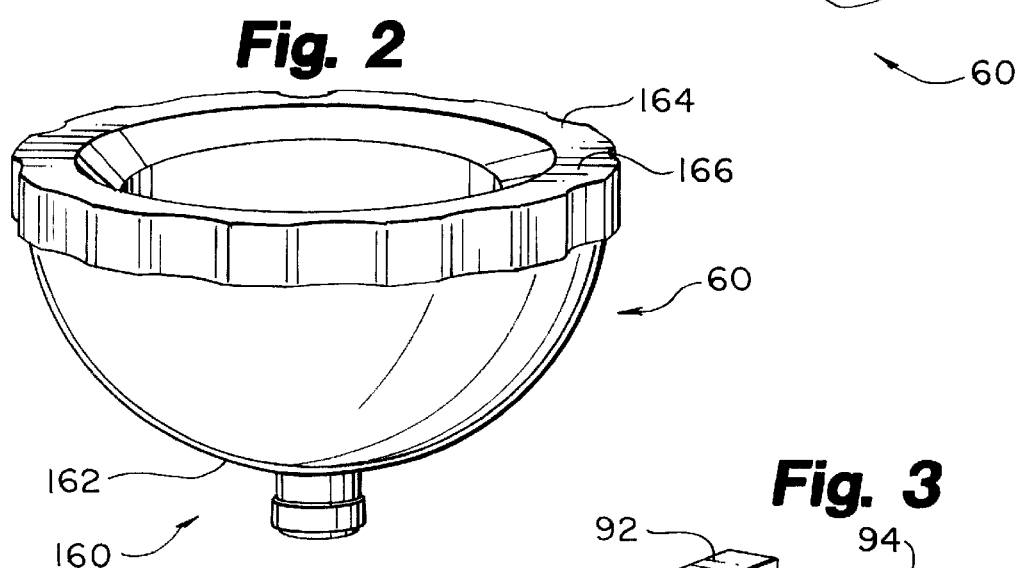
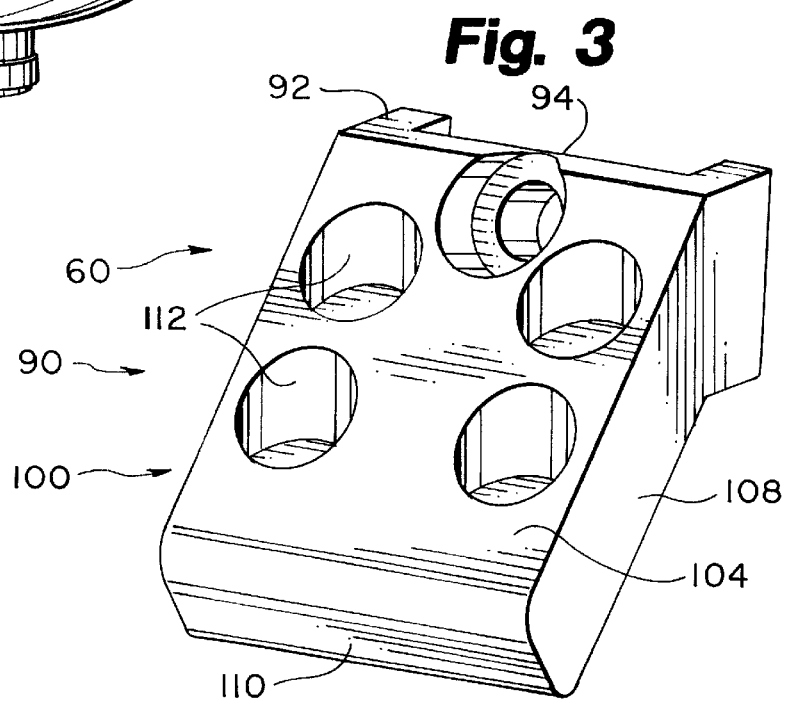

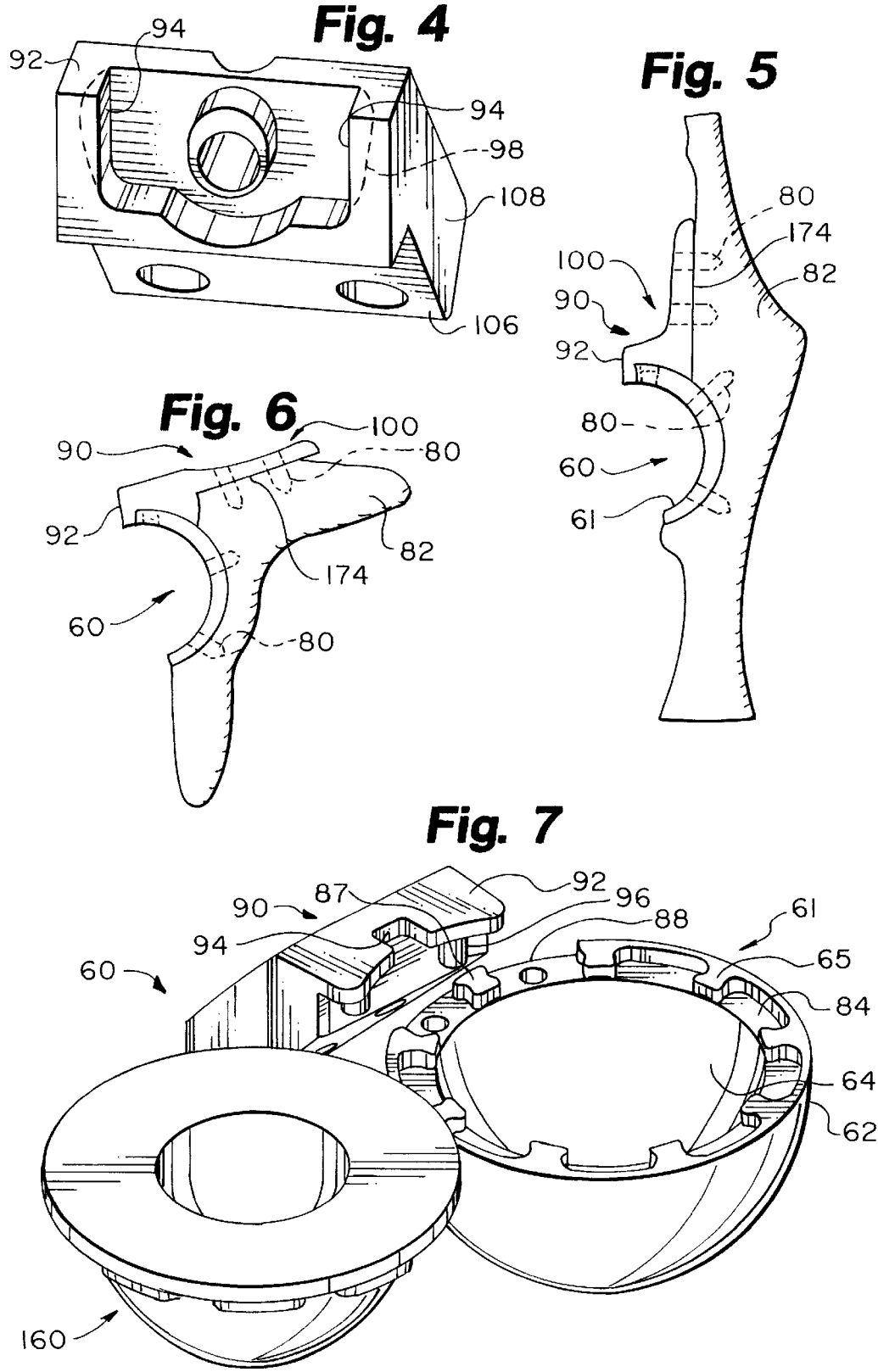

a cup-shaped body portion,
an extension, and a liner. The extension connects to the
cup-shaped body portion and is preferably produced at a
selection of angles suited to various acetabular defects. The
body portion and extension are secured to the bone, and the
liner is inserted within the body portion. Those surfaces of
the body portion and extension contacting the surface of the
bone are preferably controlled-porosity surfaces with coatings of bone-growth enhancing agents.

ACETABULAR CUP PROSTHESIS WITH EXTENSION FOR DEFICIENT ACETABULUM

RELATED APPLICATION

This application claims the benefit of U.S. Provisional Application No. 60/063,905, filed Oct. 31, 1997.

FIELD OF THE INVENTION

The present invention relates to orthopedic prosthetic implants, and more particularly to an acetabular cup prosthesis for use as both a primary implant and a revision implant.

BACKGROUND OF THE INVENTION

Acetabular cup prostheses are used in correcting numerous types of acetabular defects. Each defect often presents a different problem such as a deficient host bone or a compromised acetabular wall. Specific hip conditions present other particular problems. For instance, in the case of a revision hip replacement, the surgeon is often faced with an isolated superior defect, an isolated posterior defect, or a combined superior-posterior defect. This bone defect occurs during the process of loosening of the previous prosthesis or during the revision operation when bone cement is being removed. In the case of congenital hip dysplasia, the surgeon is faced with an extremely shallow acetabulum but must try to maximize the stability of the prosthesis, i.e., ream the acetabulum without violating the medial acetabular wall. In the case of acetabular fractures, the surgeon is often faced with a socket that has or will heal in a deformed shape. And, in the case of infection, the surgeon sees the result of the infection as bone loss that produces a deformed and/or deficient acetabulum.

In view of the above-described various bone defects, numerous prostheses have been created including devices for filling bony defects. The prosthesis must be stably seated so that it will not shift or loosen. In the case of a conventional cup-shaped prosthesis, the cup must be embedded deeply enough into the bone so that it will be stable. The cup-shaped prosthesis must be selected with a diameter large enough to span the widest part of the defect and also to be stably imbedded; the larger the prosthesis diameter, the greater the amount of reaming that is typically required. Thus significant reaming is often required to embed the prosthesis; unfortunately, reaming often removes viable bone as well as diseased bone.

SUMMARY OF THE INVENTION

There is a need for an acetabular cup prosthesis that accommodates numerous shapes and sizes of defects while at the same time minimizing the amount of bone that must be removed. This invention discloses a means for stabilizing the prosthesis with an extension that is attached to the prosthesis and anchored to the bone. Use of an extension allows for new methods and designs for optimally placing and stably imbedding the prosthesis. A modular system allows for a wide variety of defects to be optimally accommodated with a limited number of system components. A prosthesis tailored to the particular anatomy of each patient is anticipated to improve the long-term survival of the prosthesis compared to the conventional one-approach-fits-all technique.

The acetabular cup prosthesis invention has an extension allowing customization of the fit and stability of an acetabular cup in deficient acetabulae while minimizing the reaming of good bone around the deficiency. The acetabular cup prosthesis generally comprises a cup-shaped body portion, an extension, and a liner. The extension connects to the cup-shaped body portion and is preferably produced at a selection of angles suited to various acetabular defects. The body portion and extension are secured to the bone, and the liner is inserted within the body portion. Those surfaces of the body portion and extension contacting the surface of the bone are preferably controlled-porosity surfaces with coatings of bone-growth enhancing agents.

DESCRIPTION OF THE DRAWINGS

FIG. 1 depicts an acetabular cup prosthesis of the present invention, designed for use with a cup-shaped body portion, a liner and an extension.

FIG. 2 depicts an exemplary liner for use with the cup of FIG. 1.

FIGS. 3 and 4 depict an extension in alternate views.

FIGS. 5 and 6 are side views of the acetabular cup prosthesis of the invention indicating the placement and alignment of the cup and extension.

FIG. 7 shows a perspective view of an exemplary acetabular prosthesis system's components; the cup-shaped body portion, the liner, and the extension.

DETAILED DESCRIPTION OF THE INVENTION

Figure 8:
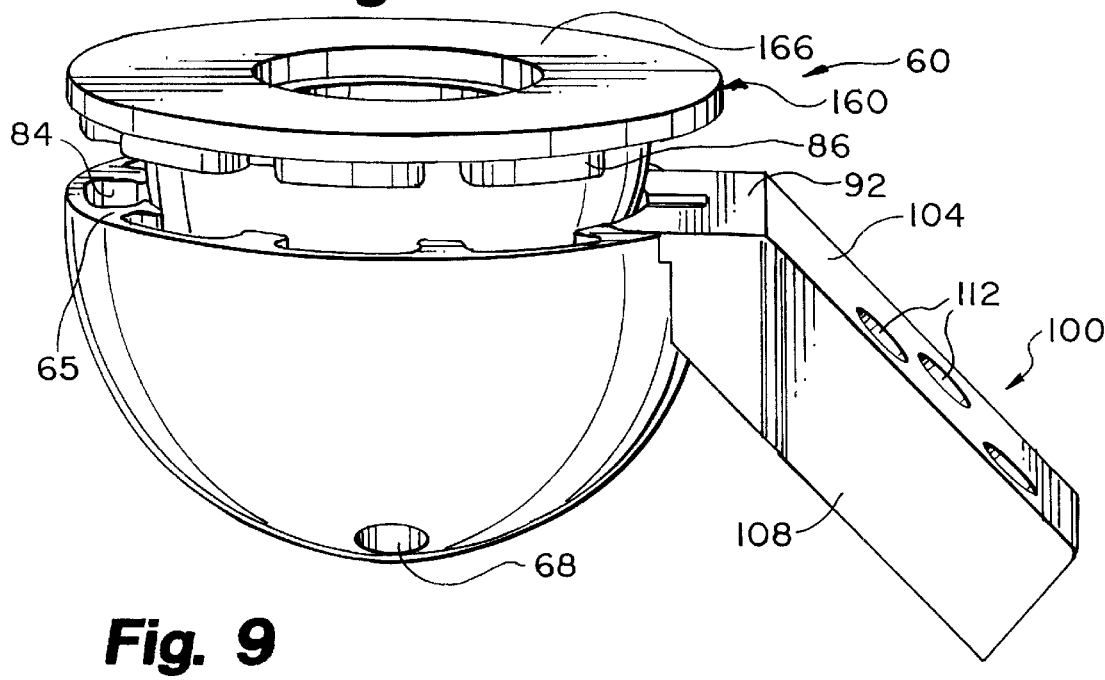
FIG. 8 is a side view of the acetabular cup prosthesis with the extension in position and having its top portion flush to the cup-shaped body portion; the mortise and tenon joints of the liner and cup-shaped body portion are aligned for interlocking.
Figure 9:
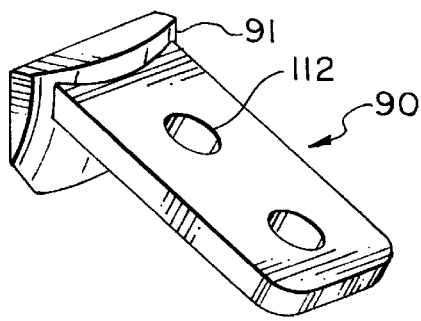
FIGS. 9–12 show a dovetail taper in combination with a mortise-and-tenon for connecting an extension to the cup-shaped body portion.
Figure 10:
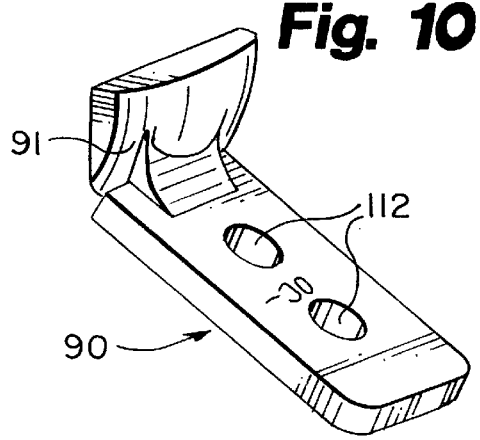

The acetabular cup prosthesis of the present invention generally includes a cup-shaped body portion, an extension and a liner.

FIG. 1 illustrates acetabular cup prosthesis 60 preferably comprising a cup-shaped body portion 61 having a convex outer surface 62, a cup wall 63 and a concave inner surface 64. An annular, substantially flat rim 65 extends around periphery 67 of body portion 61. A base plane is defined by annular rim 65.

At least one opening 68 normally extends through cup wall 63 as shown in FIG. 8, to facilitate securing of cup-shaped body portion 61 therein. Other openings in wall 63 may exist to facilitate securing of the prosthesis. A central opening at the cup apex may or may not be provided. If a central opening is provided, it generally includes a threaded surface for the removable connection of a handle to cup-shaped body portion 61 enabling easier positioning of the body portion 61 to the acetabula. Note that body portion 61 preferably has a central axis substantially perpendicular to the base plane.

In one embodiment, such as that shown in FIGS. 7 and 8, annular rim 65 of cup-shaped body portion 61 is preferably provided with a plurality of mortises 84 which fit tenons 86 of liner 160 (described below) and preferably further includes key 87 and cylindrical recesses/apertures 88 for positioning and connecting with posts 96 of extension 90. Cup-shaped body portion 61 is preferably made of a titanium alloy, e.g., T16-AL4V, or a cobalt chromium, although various known materials may be suitable. Outer surface 62 of cup-shaped body portion 61 is preferably a controlled-porosity surface to enable bone growth to prosthesis 60. Outer surface 62 may also be associated with a biologically active agent that enhances bone growth, for example, bone-morphogenetic protein, growth factors, and hydroxyapatite to encourage bone growth to prosthesis 60, although these are optional features.

Referring to FIG. 3, one embodiment of extension 90 includes upper flat surface 92, incorporating a key-way portion 94, a pair of downward extending cylindrical posts 96 (shown in FIG. 7), back portion 98, and flange 100. Back portion 98 (shown in FIG. 4) has contoured surfaces to accommodate the curvature of body portion 61 and to aid in a snug fit between extension 90 and body portion 61. Flange 100 has top face 104, bottom face 106, side edges 108 and lower edge 110. Flange 100 preferably includes a plurality of apertures 112 for insertion of bone screws 80 or other attaching means. Flange 100 and body portion 61 may be configured such that bone screw 80, or other appropriate connection means, is inserted through the body portion, flange, and into bone 82 serving as an additional means of reinforcing the connection of extension 90 to body portion 61. Extension 90, like body portion 61, is preferably made of a titanium alloy, e.g., T16-AL4V, or a cobalt chromium. Also, similarly, bottom face 106 preferably has a controlled-porosity surface and optionally incorporates biologically active agents to encourage bone growth to prosthesis 60, as described above.

Figure 14:
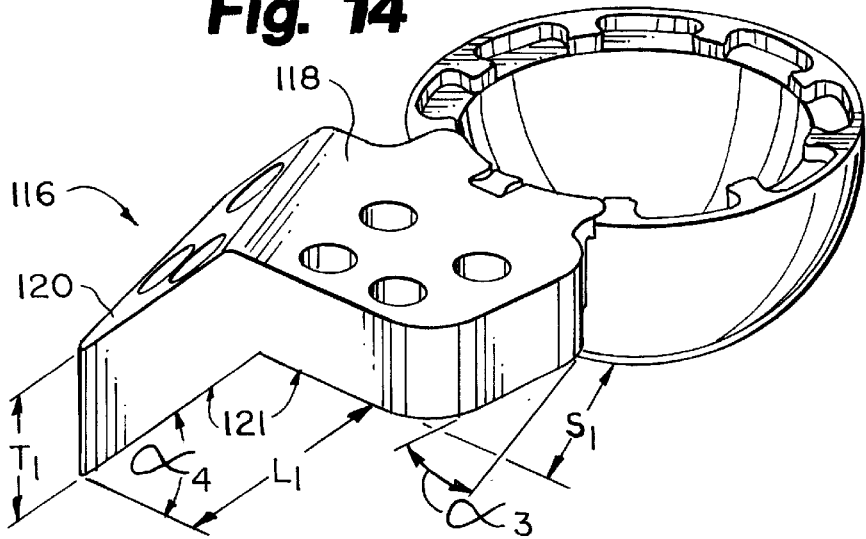
FIGS. 14–16 depict various geometries of an extension and their connection to the cup-shaped body portion.
Figure 15:
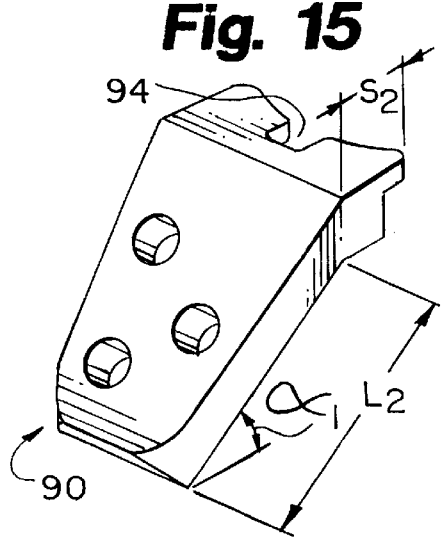
Figure 16:
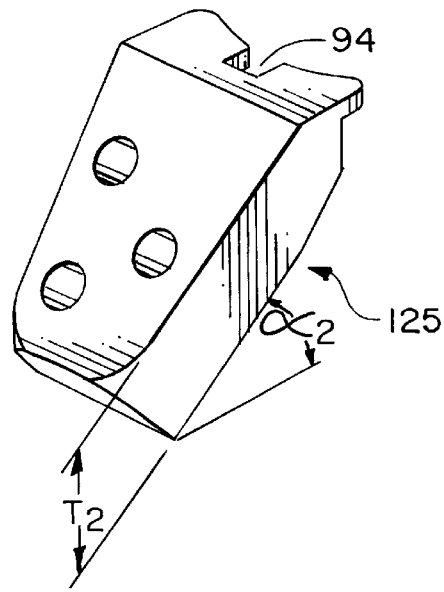

Extension 90 is preferably produced in a limited number of geometries or angles (e.g. $\alpha_1$, $\alpha_2$, $\alpha_3$, $\alpha_4$ shown in FIGS. 14 through 16) of bottom face 106 relative to cup 61 to reduce the number of extensions 90 that must be stocked and fitted per patient. For instance, extension 90, for a superior defect, is preferably produced for every five or 10 degrees in an appropriate range, such as 30 to 60 degrees. Alternatively, only a few or even only one angle of extension 90 might be produced at a convenient angle appropriate for a number of defects, such as 45 degrees. Extensions 90 are similarly produced and stocked for posterior defects in an appropriate range, such as 60 to 90 degrees. Body portions 61 are preferably produced in limited but varying sizes to accommodate various bony defects. Note that, because of the modularity of the prosthesis and the various angles of the extension, smaller body portions 61 (or shells) may be used because it is unnecessary to ream to a larger diameter to accommodate the bony defect; instead, extension 90 virtually accommodates the bone defect. The result is the salvage of more host bone and the reduction of reaming necessary to achieve stability. Preferably an extension-to-body portion connection will be used whereby the extensions obviate the need for larger cup sizes and therefore may result in fewer production sizes of cup-shaped body portions being required, with the advantageous reduction in bone removal due to the use of smaller sized cups.

Regardless of the angle of extension 90, extension 90 itself is designed to position and connect appropriately to cup-shaped body portion 61. Various means for achieving this connection are contemplated. In one embodiment, shown in FIG. 7, cylindrical posts 96 are designed to slide into cylindrical apertures/recesses 88 until upper flat surface 92 is substantially flush with annular rim 65 and key-way portion 94 is placed around key 87 of body portion 61. While the figures depict the use of a single extension, the use of multiple extensions or a single multi-directional extension that extends outward from the circumference of body portion 61 is easily comprehended with the modification of additional cylindrical apertures/recesses 88 and keys 87 in body portion 61. Further, the idea of accommodating a varied defect may also be achieved. As shown in FIG. 14, side angle extension 116 may have a top plate 118 and a flange 120 that present a compound or multi-planar bottom face 121 relative to the cup, and with bottom face being most appropriate for attachment to the bony defect. As further shown in FIGS. 14, 15, and 16, various extensions 116, 90, 125 may vary in thickness ($T_1$, $T_2$), length ($L_1$, $L_2$), and/or standoff ($S_1$, $S_2$).

Figure 11:
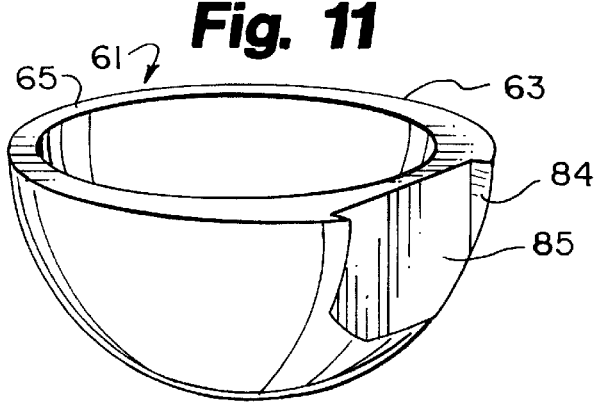
Figure 12:
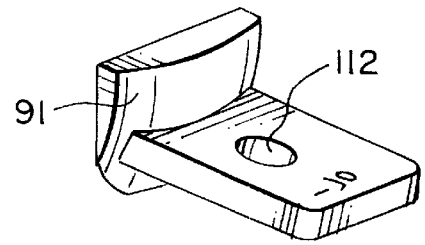

FIGS. 11 and 12 show another embodiment of the connection between the extension and the cup-shaped body portion. Cup-shaped body portion 61 has a mortise with a taper 85. The mortise is the shape of a wedge and mates with wedge-shaped tenon 91. The mortise and tenon fit snugly and may be further secured by a screw (not shown) or by making the joint with a shape memory alloy so that the joint is made more snug when the joint reaches body temperature. The extension may have openings 112 for use with screws or other means of anchoring the extension to bone.

Similarly, FIGS. 1, 3, and 4 show another embodiment of the connection between the extension and the cup-shaped body portion. The body portion comprises connecting face 69 that is set apart from outer surface 62 by configured surfaces or grooves 70. The connecting face may either project out from surface 62 or be consistent with the curvature of the outer surface. The connecting face is shown to be surrounded on three sides by key-way portion 94 of extension 90 but may also be surrounded on four sides; for instance, by moving the connecting face down towards the apex of the body portion and making grooves 70 describe more of a rectangular shape.

This use of a connecting face exemplifies a means of making a modular system wherein the different portions of the acetabular cup prosthesis are readily interchangeable. The connecting face and the grooves may be made with a standard shape and size so that an extension may be readily connected to a wide range of body portion sizes, regardless of diameter or curvature considerations. Further, other elements may be introduced to create a fully modular system. For instance, a crossover flange might be used to adapt some of the cup-shaped prostheses to a standardized extension connection.

A modular system may be further realized by making the extensions themselves from modular components. The extensions may be assembled from interchangeably connectable modular components so that a great variety of shapes of extensions may be generated from a few extension components.

Figure 13:
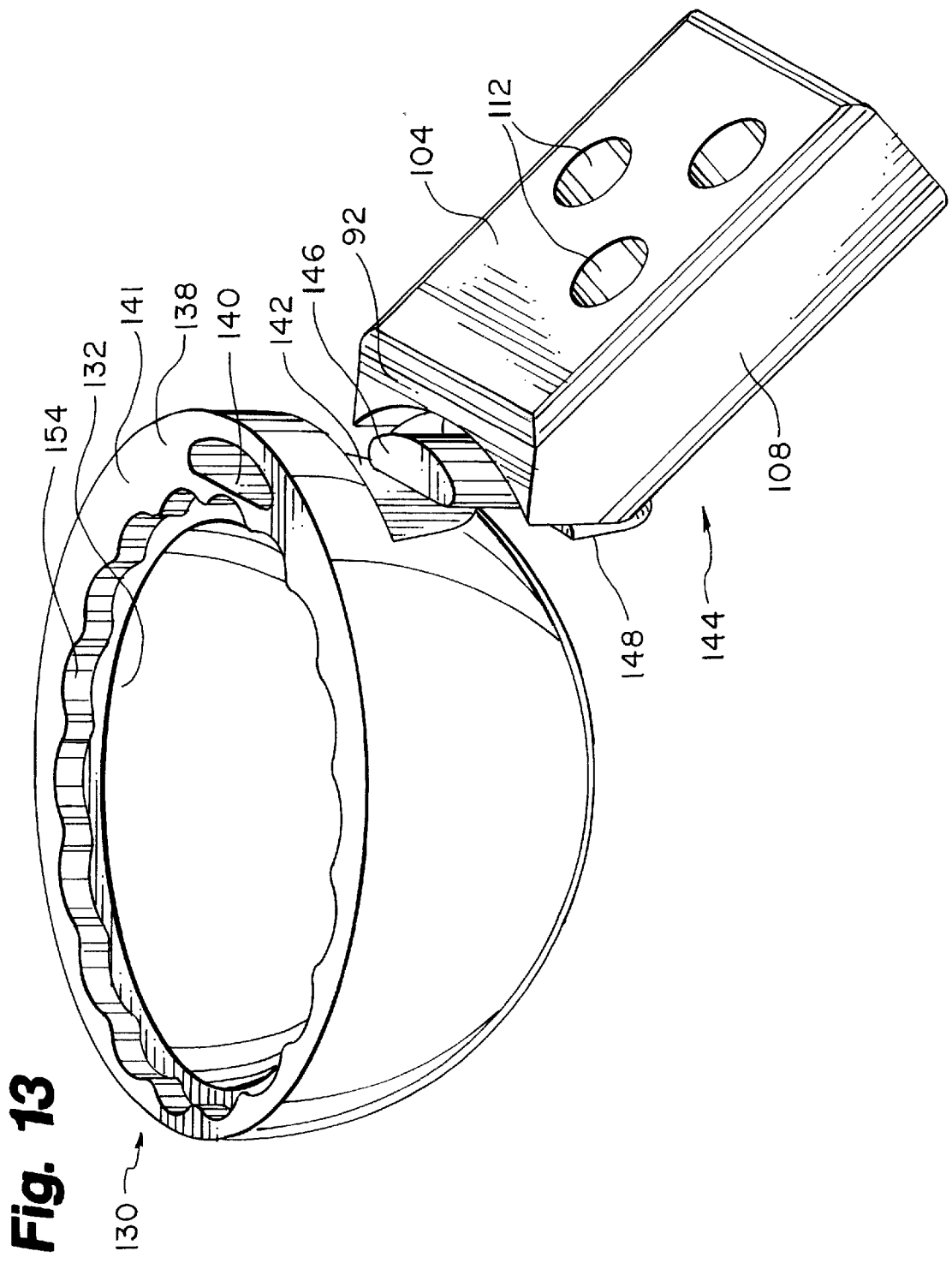
FIG. 13 shows an acetabular cup prosthesis with a lug-and-bore connection to an extension; further, the cup-shaped body portion accommodates a non-central placement of the liner and the thickened portion of the body-portion wall comprises the connecting means.

FIG. 13 shows another embodiment of a connection between cup-shaped body portion 130 and extension 144. In this instance, body portion 130 is preferably substantially spherical in shape such that the internal cup-shaped portion 132 is maintained with a center offset from the central axis of body portion 130. As such, offset portion 138 exists and is provided with slot 140 for positioning of extension 144.

Slot 140 extends through rim 141 to sectioned area 142, which is a section of offset portion 138 that has been removed or left open. Extension 144 includes post 146 sized to accommodate slot 140. Preferably, unitary with post 146 is a mating sectioned area 148 designed to fit within sectioned area 142. Body portion 130 is optionally provided with scalloped edge 154 to receive and position an appropriately mated liner. The same materials, surfaces and coatings appropriate to body portion 61 and extension 90 are equally appropriate to body portion 130 and extension 144. It is recognized that offset designs of cups may be appropriate for one or both inner or outer surfaces, or no surfaces at all, as requested.

Yet another embodiment of the invention comprises extensions 90, 144 made of a Shape Memory Alloy (SMA) including, for the purposes of this application, the nitinol property of super-elasticity. Upon warming to body temperature, extensions 90, 144 conform to the shape of the underlying bone 82. The various extensions 90, 144 may be configured with surface protrusions or similar means for encouraging bone ingrowth to occur, for example, extensions 90, 144 could have a porous or mesh backing.

Use of SMA materials in acetabular cup prostheses entails careful prediction of forces that will be applied to the acetabulum and other bones near the surgical site. Indeed, undesired forces on the bone from contact with acetabular cup extensions may induce bone fracture or cup displacement. This is particularly relevant to revision hip replacement surgery in which there is likely a pre-existing bone structural weakness. In one embodiment of the invention, at least one shape memory metal extension 90, 144 of body portion 61, 130 is matched for use in a recipient site. The entire prosthesis 60 is cooled, and extension 90, 144 is retracted from its "memory" position. A memory position may include a predicted average angle for superior and posterior defects, as well as other angles. This may be accomplished by imaging or other visualization or predictive means, which may include machine implemented methods, steps or algorithms. Then body portion 61, 130 is oriented at the site and appropriately secured to bone 82. Extension 90, 144 is then warmed by either the patient's body heat or other means until they have reshaped into their memory positions. If the memory position has been designed correctly, then extension 90, 144 will always contact bone 82 just before the memory position. This ensures that a sufficient, but minimal, force will be generated upon contact of extension 90, 144 to bone 82. Use of an extension system also allows for selection of the best final positions of each extension 90, 144 according to the particular morphology of each recipient site, and allows for bone screws 80 or other final attaching means to be used at the regions of harder or thicker bone. Extensions 90, 144 may optionally attach to body portion 61, 130 using a shape memory material configured as a ring or split ring designed to attach to a circumferential portion of body portion 61, 130. Indeed, many forms of connecting an extension to a body portion using shape memory material as a connecting means may provide stronger attachment than any other means.

Liner 160, shown in FIGS. 2, 7 and 8, is preferably of an ultra-high molecular weight polyethylene material. Liner 160 has an outer cup-shaped surface 162 designed to fit within body portion 61, inner cup-shaped surface 164, rim 166, and, optionally, a plurality of tenons 86. Tenons 86 are designed to dovetail with mortises 84 of body portion 61. A gap may be provided between tenons 86 to accommodate extension 90. While the above embodiment of liner 160 utilizes a mortise and tenon joining means, other types of joining means may be appropriate as well. For instance, liner 160 may incorporate a scalloped edge to accommodate scalloped edge 154 of body portion 130, as well as other means.

A variety of extension geometries are needed to accommodate a wide variety of acetabular deficiencies. For instance, in the case of a revision hip replacement, the surgeon is often faced with an isolated superior defect, an isolated posterior defect, or a combined superior-posterior defect. Therefore, extensions with a geometry like that embodied in FIG. 14 may be useful. Extension 116 has a first portion 118 that extends directly away from the axis of the body portion and a second portion that descends down and away from the first portion. The possible geometries include extensions with various thicknesses, curves, or other shapes.

Figure 17:
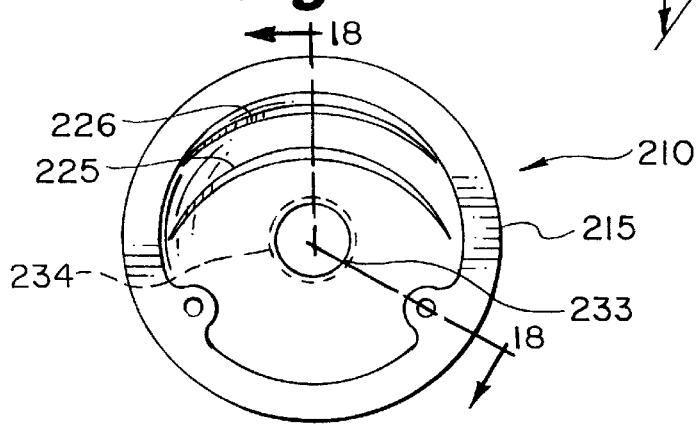
FIGS. 17 and 18 depict a cutting guide in different views.
Figure 18:
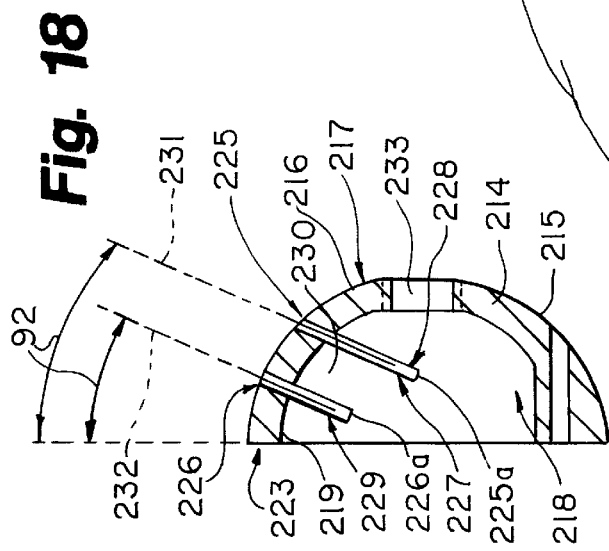

A cutting guide sized according to the desired prosthesis size may be used to clean the implant site and to create an optimally-sized seat for the prosthesis, i.e. the cups diameter does not have to be made larger to accommodate the defect. The extension allows the diameter of the cup to be smaller than during prior procedures where a larger cup (and more bone removal) was needed. Exemplary cutting guide 210 is shown in FIGS. 17 and 18. Cup-shaped guide 210 may have a cutting or abrasive surface that contacts the bone. The guide may be pressed and rotated against the bone to remove bone, old cement, or other undesired material. The guide and cutter are pre-set to cut at the proper angle for each extension. Further, the cutting guide could be used merely to mark the bone for removal with other surgical tools.

Figure 19:
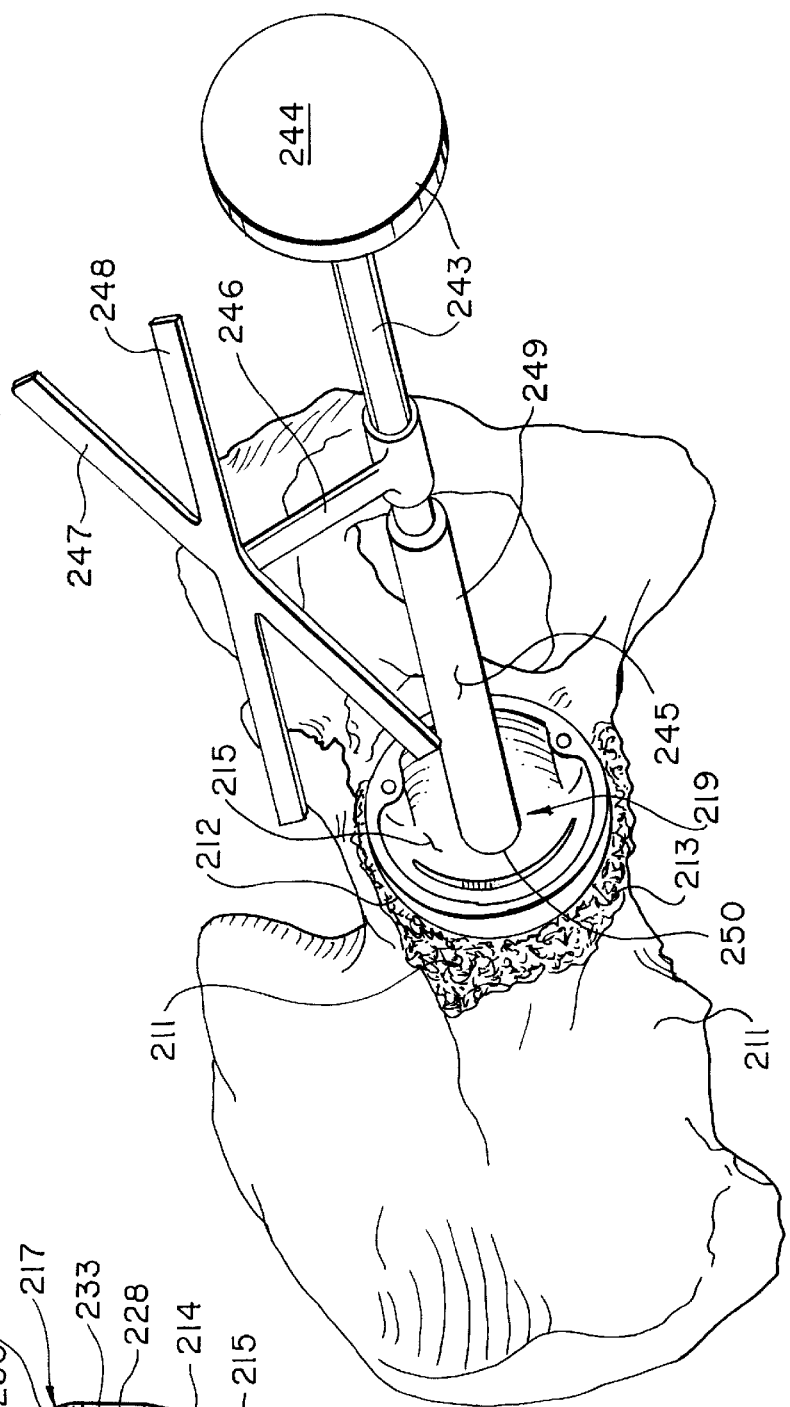
FIG. 19 shows a cutting guide equipped with an alignment handle.

For example, FIGS. 17–19 show cutting guide 210 that can be used to cut the patient's pelvic anatomy 211 during revision acetabular cup prosthesis implantation. The patient's pelvic anatomy 211, diseased acetabulum 212, and reamed acetabulum 213, are shown. Cutting guide 210 includes cup-like body 215 having a first side 216 that presents a curved convex surface 217. Recess or open area 218 is provided on the side of prosthesis body 215 opposite convex surface 217. This open area 218 communicates with concave surface 219 of body 215.

Cup body 215 has a pair of cutting guide slots 225, 226. Each of the slots 225, 226 is closed at one end 225A, 226A to accommodate blades. Each of the cutting guide slots 225, 226 is comprised of a pair of generally parallel flat surfaces and is bordered by a pair of flat parallel surfaces 229, 230. Each of the cutting guide slots 225, 226 defines cutting plane, 231 or 232. Opening 233 in cup wall 214 can be internally threaded for attachment of alignment handle 243. Opening 233 has internal threads 234 for receiving a similarly, externally-threaded portion of the distal end of shaft 245 of handle 243.

Handle 243 can be threadably be attached to internal threads 234 of opening 233. The surgeon can then grip handle 243 to align and manipulate the position of cup body 215 as desired. The surgeon can then disconnect handle 243 by simply unthreading shaft 245 from internally-threaded opening 233 of guide body 215. Handle 243 has an enlarged proximal end 244, a linear shaft portion 245, a transverse strut 246, and a pair of laterally extending handle members 247, 248. Sleeve 249 surrounds the lower end of shaft 245, and can be knurled if desired for gripping. Distal end 250 of handle 243 is externally threaded, providing a thread pattern that engages the internal threads 234 of opening 233. The handle may be adapted for use with either the cutting guide or the cup-shaped body portion of the prosthesis.

In using acetabular cup prosthesis 60, a surgeon reams out a deficient acetabulum with instrumentation so that, in some embodiments, bone 82 presents a standard defect, or in other words, a defect presenting a substantially flat surface 174 at a desired angle, e.g., 45 degrees for a superior defect or perhaps 70 degrees for a posterior defect, for example as illustrated in FIGS. 5 and 6. Bone 82 is reamed to a desired angle to accommodate an angle of stocked extension 90. More generally, however, the extensions will likely be set to a first angle for superior defects, a second angle for posterior defects, and the variable will be the different depths of reaming. This presents a simpler method using improved tools and techniques. This substantially eliminates the need to attempt to find a prosthesis to fit a particular bone defect and also reduces the amount of reaming that is necessary, e.g., bone 82 need only be reamed to the closest extension angle and depth, using a cup sized much smaller than was required in past revision surgeries.

Once reaming of bone 82 is complete, an appropriately-sized, cup-shaped body portion is selected. Extension 90, 144 is selected, connected to body portion 61, 130 and secured to bone 82 by appropriate attachment means. Cup-shaped body portion is also affixed to the site. Liner 160 is then placed in position within body portion 61, 130.

It is recognized that considerable advantage can still be accomplished using the above concepts with one or more extensions 90, 144 that are unitarily manufactured with body portion 61, 130. However, greater flexibility, stocking efficiencies, and other considerations are often optimized with a modular or semi-modular system. A semi-modular system may comprise, for example, one or more extensions which are connected to a locking ring or similar mechanism suitable for selection and attachment to body portion 61 during surgery.

Because many varying and different embodiments may be made within the scope of the inventive concept herein taught, and because any modifications may be made in the embodiments herein detailed in accordance with the descriptive requirement of the law, it is to be understood that the details herein are to be interpreted as illustrative and not in a limiting sense; reference being made to the appended claims to determine the scope of the invention.

One example of such alternate embodiments includes a rotatable extension configuration as shown in the phantom lined wall portions of FIG. 4. This wall shaping, along with other easing of certain wall shapes, allows for a rotatable embodiment to further accommodate various morphologies. This embodiment may be particularly advantageous with shape memory alloy connecting means to the associated cup.

Yet another example of alternate embodiments includes the use of cup 61 in either revision or primary surgery. This embodiment, in which only a small fraction of the outer surface 63 is removed at 70 to accommodate extension attachment, is designed to maintain adequate surfaces to properly function as a primary cup. No known prosthesis is suitable for both types of surgeries, with all the other advantages described herein.

What is claimed:

1. An acetabular cup prosthesis for use in a patient's deficient acetabulae, the prosthesis comprising:
    a body portion having an axis and a rim tangent to a base plane that is substantially perpendicular to said axis;
    connecting means for connecting an extension to said body portion; and
    wherein one or more components of the prosthesis includes a shape memory alloy.

2. The prosthesis of claim 1 in which the extension comprises means for connecting to a portion of the body portion, a standoff portion and a length portion, the extension having a bottom face configured at a select angle relative to the body portion base plane for contact with the patient's acetabulae region and to provide additional support to the prosthesis.

3. The prosthesis of claim 1, wherein the body portion comprises an inner and an outer surface, and wherein the connecting means is configured to connect to at least one extension that contacts the outer surface.

4. The prosthesis of claim 3, wherein the connecting means comprises a shape memory alloy.

5. The prosthesis of claim 3, wherein the connecting means comprises at least one opening.

6. The prosthesis of claim 5, wherein the opening comprises threads.

7. The prosthesis of claim 5, wherein the connecting means are partially disposed on the outer surface.

8. The prosthesis of claim 5, wherein at least one of the openings comprises a notch.

9. The prosthesis of claim 8, wherein at least one of the openings comprises a slot.

10. The prosthesis of claim 5, wherein at least one of the opening(s) passes through the outer surface and extends at least partially through the body portion.

11. The prosthesis of claim 10, wherein the openings comprise surfaces comprising a shape memory alloy.

12. The prosthesis of claim 3, wherein the connecting means comprises a raised portion comprising openings.

13. The prosthesis of claim 3, wherein the connecting means does not protrude from the outer surface.

14. The prosthesis of claim 3, wherein the connecting means comprises grooves in the outer surface, whereby the grooves may be mated with a reciprocally designed extension portion.

15. The prosthesis of claim 14, wherein the connecting means comprises at least one opening.

16. The prosthesis of claim 14, wherein the connecting means are at least partially disposed in the rim.

17. The prosthesis of claim 16, wherein the connecting means comprise openings in the rim and in the outer surface.

18. The prosthesis of claim 6, wherein the connecting means are at least partially disposed in the rim.

19. The prosthesis of claim 18, wherein the connecting means in the rim comprise protuberances.

20. The prosthesis of claim 18, comprising a stabilizing space, the space defined by the open surface area between an extension and the rim, the space being made by choosing the position of the connecting means, whereby the space allows for improved stabilization of the prosthesis by permitting osseo-integration between the extension and the rim.

21. The prosthesis of claim 1 comprising biologically active agents whereby osseo-integration of the prosthesis with the acetabulae may be improved.

22. An acetabular cup prosthesis for use in deficient acetabulae, the prosthesis comprising;
    a body portion having an axis and a rim, the rim tangent to a base plane that is perpendicular to the body portion's axis;
    an extension comprising a top surface and a bottom surface;
    wherein the body portion and the extension are connected by a connecting means;
    whereby the extension has a first angle, the first angle being formed between the base plane and a first line, the first line having a first point at the intersection of the extension with the body portion and a second point at the opposite end of the extension, with both the first and the second point located in the middle of the extension's bottom surface; and so that the extension has a second angle that is perpendicular to the first angle, the second angle being formed between the first line and a plane containing the body portion axis and the first point; and wherein one or more components of the prosthesis includes a shape memory alloy.

23. The prosthesis of claim 22, wherein the connecting means comprises a shape memory alloy.

24. The prosthesis of claim 22, wherein the connecting means comprises interlocking means.

25. The prosthesis of claim 24, wherein the interlocking means comprises at least one mortise-and-tenon combination.

26. The prosthesis of claim 24, wherein the connecting means comprises at least one bore-and-lug combination.

27. The prosthesis of claim 26, wherein the bore-and-lug combination comprises a threaded connection.

28. The prosthesis of claim 22, wherein the extension comprises surfaces defining openings for connecting means whereby the extension may be affixed to a patient's bone.

29. The prosthesis of claim 22, wherein the first angle has an absolute value in the range of 15 to 120 degrees.

30. The prosthesis of claim 29, wherein the second angle has an absolute value in the range of 0 to 180 degrees.

31. The prosthesis of claim 22, wherein the extension comprises a first and a second portion, the first portion contacting the body portion and substantially parallel to the base plane and being continuous with a second portion that descends from it at an angle, whereby the first and the second angle are non-zero so that a combined superior and posterior defect may be fitted.

32. The prosthesis of claim 22 comprising more than one extension.

33. The prosthesis of claim 32 comprising tabs extending from the body portion, whereby the tabs may be used to stabilize the body portion within the bone.

34. The prosthesis of claim 33, wherein the tabs comprise shape memory alloy.

35. The system of claim 22, wherein the extension is comprised of extension modular parts, each extension modular part being interchangeably connectable to form an extension.

36. An acetabular cup prosthesis for use in deficient acetabulae, the prosthesis comprising:

a cup-shaped body portion having a central axis, an inner surface, an outer surface, and a rim tangent to a base plane;

an extension, the extension comprising mechanical means for connecting to the body portion;

a liner, the liner being insertable into the body portion and comprising a lip that rests substantially on the body-portion's rim;

the liner and the body portion farther comprising a connecting means whereby they may be connected; and wherein one or more components of the prosthesis includes a shape memory alloy.

37. The prosthesis of claim 36, wherein the connecting means comprises a shape memory metal.

38. The prosthesis of claim 36, wherein the inner surface of the body portion is substantially concave and defines an inner-surface central axis and the outer surface is substantially convex and defines an outer-surface axis; wherein the inner-surface axis and the outer-surface axis are offset, whereby the body portion has an area of increased wall thickness.

39. The prosthesis of claim 38, wherein the area of increased wall thickness comprises at least a portion of the mechanical means for connecting the body portion and the liner.

40. The prosthesis of claim 38, wherein the lip comprises means for accommodating an extension that is connected to the rim of the body portion.

41. A modular acetabular cup prosthesis system for use in deficient acetabulae, the system comprising;

a selection of cup-shaped body portion units, each cup-shaped body portion unit having a central axis, an inner surface, an outer surface, and a rim tangent to a base plane;

a selection of extension units, each extension unit comprising mechanical means for connecting to a body portion unit;

a selection of liner units, each liner unit being insertable into a body portion unit and comprising a substantially concave inner surface, a substantially convex outer surface, and a lip that rests substantially on the body-portion unit's rim;

each liner unit and body portion unit further comprising a connecting means whereby they may be connected;

whereby the extension has a first angle, the first angle being formed between the base plane and a first line, the first line having a first point at the intersection of the extension with the body portion and a second point at the opposite end of the extension, with both the first and the second point located in the middle of the extension's bottom surface;

so that the extension has a second angle that is perpendicular to the first angle, the second angle being formed between the first line and a plane containing the body portion axis and the first point;

wherein the first angle has an absolute value in the range of 15 to 120 degrees and the second angle has an absolute value in the range of 0 to 180 degrees;

whereby the system enables rapid and economical assembly of an optimally-shaped acetabular cup prosthesis by choosing a liner unit, a body portion unit, and an extension unit; and wherein one or more components of the prosthesis includes a shape memory alloy.

42. The system of claim 41 further comprising a selection of cutting guides, the cutting guides comprising a means for removing bone and creating a cavity sized to snugly fit a body portion.

43. The system of claim 41, wherein approximately each unit is interchangeably connectable to the other types of units;

whereby liner units of various inner diameters may each be connected to approximately any body portion unit, and any extension unit may be connected to approximately any body portion unit.

44. The system of claim 41, wherein each extension unit connects to the body portion with a limited variety of well-defined geometries so that a cutting guide template may be chosen, whereby the appropriate template may be easily selected.

45. The system of claim 41 comprising means for the body portions to receive liners with a variety of shapes and sizes.

46. The system of claim 41, wherein the extension units are comprised of extension modular parts, each extension modular part being interchangeably connectable to form an extension.

47. A method of sizing and implanting an acetabular cup prosthesis in a patient, the method comprising;

attaching at least one extension to a cup-shaped portion of an acetabular prosthesis, the cup-shaped portion comprising an inner surface with a central axis, an outer surface, and a rim;

implanting the prosthesis in the patient;

wherein the extension is configured to contact the outer surface of the cup-shaped portion of the prosthesis and extends away from its axis; and wherein one or more components of the prosthesis includes a shape memory alloy.

48. The method of claim 47 comprising the step of cutting the bone of the patient to achieve a geometry suitable for accommodating said extension.

49. The method of claim 47, wherein the step of attaching the extension to the cup-shaped portion takes place after the cup-shaped portion has been secured to the bone of the patient.

50. The method of claim 48 comprising the step of using an alignment handle to manipulate the prosthesis, wherein the handle is removably connected to the cup-shaped body portion of the prosthesis.

51. A method of implanting an acetabular cup prosthesis in a patient, the method comprising;

attaching at least one extension to a cup-shaped portion of an acetabular prosthesis, the cup-shaped portion comprising an inner surface with a central axis, an outer surface, and a rim;

cutting the bone to achieve a geometry suitable for accommodating said extension;

implanting the extension in the patient;

wherein the extension contacts the outer surface of the cup-shaped portion of the prosthesis and extends away from its axis; and wherein one or more components of the prosthesis includes a shape memory alloy.

52. The method of claim 51, wherein the extension is attached to an acetabular prosthesis implanted in the patient during a previous surgery.

* * * * *